US007696899B2

(12) United States Patent
Immerz et al.

(10) Patent No.: US 7,696,899 B2
(45) Date of Patent: Apr. 13, 2010

(54) MARKER NAVIGATION DEVICE

(75) Inventors: Martin Immerz, Gräfelfing (DE); Gregor Tuma, Munich (DE)

(73) Assignee: BrainLAB AG, Feldkirchen (DE)

( * ) Notice: Subject to any disclaimer, the term of this patent is extended or adjusted under 35 U.S.C. 154(b) by 364 days.

(21) Appl. No.: 11/872,737

(22) Filed: Oct. 16, 2007

(65) Prior Publication Data

US 2008/0119726 A1 May 22, 2008

Related U.S. Application Data

(60) Provisional application No. 60/862,878, filed on Oct. 25, 2006.

(30) Foreign Application Priority Data

Oct. 20, 2006 (EP) ................................. 06122639

(51) Int. Cl.
*G08B 1/08* (2006.01)
*G08B 5/22* (2006.01)
*G01S 3/02* (2006.01)

(52) U.S. Cl. ........................ 340/825.36; 340/825.49; 340/539.13; 342/453

(58) Field of Classification Search ... 340/568.1–572.9, 340/500, 501, 524, 525, 539.13, 10.1–10.6, 340/825.36, 825.49; 342/450, 453, 454, 342/455

See application file for complete search history.

(56) References Cited

U.S. PATENT DOCUMENTS 5,959,568 A * 9/1999 Woolley ...................... 342/42

(Continued)

FOREIGN PATENT DOCUMENTS

DE 196 39 615 4/1998

(Continued)

*Primary Examiner*—Jennifer Mehmood
(74) *Attorney, Agent, or Firm*—Renner, Otto, Boisselle & Sklar, LLP

(57) ABSTRACT

A marker navigation device for determining and/or tracking a location of a marker device is provided. The marker device is attachable to an object, said marker device including a plurality of markers having known dimensions and being in a known positional relationship relative to each other. The marker navigation device includes: a detection device operative to detect signals emitted by or reflected from the plurality of markers, wherein the detection device is formed such that in first locations of the detection device relative to the marker device, detection of signals from one marker of the plurality of markers is restricted or impossible due to a location of another marker of the plurality of markers. In second locations of the detection device relative to the marker device, the plurality of markers are detectable by the detection device. The navigation device also includes a processing device communicatively coupled to the detection device and configured to calculate the first locations based on the relative locations of individual markers of the plurality of markers and based on the known dimensions of the plurality of markers, and calculate an actual location of the marker device relative to the detection device based on detected signals from at least one marker of the plurality of markers, the known locations of the plurality of markers relative to each other, and the known dimensions of the plurality of markers. The processing device also can determines whether the actual location of the marker device is one of the first locations. A warning device is communicatively coupled to the processing device and operative to output a warning signal when the actual relative location is one of the first relative locations.

14 Claims, 2 Drawing Sheets

U.S. PATENT DOCUMENTS

| | | | |
|---|---|---|---|
| 6,348,856 B1 * | 2/2002 | Jones et al. | 340/10.1 |
| 6,351,659 B1 | 2/2002 | Vilsmeier | 600/407 |
| 6,456,239 B1 * | 9/2002 | Werb et al. | 342/463 |
| 6,466,815 B1 | 10/2002 | Saito et al. | 600/429 |
| 2006/0142657 A1 | 6/2006 | Quaid et al. | 600/424 |

FOREIGN PATENT DOCUMENTS

| | | |
|---|---|---|
| EP | 1 645 228 | 4/2006 |

\* cited by examiner

MARKER NAVIGATION DEVICE

RELATED APPLICATION DATA

This application claims priority of U.S. Provisional Application No. 60/862,878 filed on Oct. 25, 2006, which is incorporated herein by reference in its entirety.

FIELD OF THE INVENTION

The present application relates to a marker navigation device for detecting a marker means in a medical workspace, and determining a location of movable objects to which the marker means is attached.

BACKGROUND OF THE INVENTION

Currently, marker means are detected via a detection means (e.g., a camera or ultrasound detector). The marker means typically include three markers that are arranged in a fixed and predetermined location relative to each other and are in particular mechanically connected to each other. The markers attached to the marker means can be passive or active markers, wherein passive markers reflect waves and/or radiation emitted in their direction, and active markers are themselves the origin of the radiation and/or waves. The signals emitted from the (active or passive) markers, which can be wave signals or radiation signals, are detected by a detection device (e.g., a camera).

In order to establish an initial position of the marker means relative to the detection means, the marker means may be moved to provide the detection means with different views of the marker means. On this basis, the location of the marker means relative to the detection means can be determined in a known way, in particular in a spatial reference system. Reference is made in this respect to DE 196 39 615 A1 and the corresponding U.S. Pat. No. 6,351,659, each of which are hereby incorporated by reference in their entirety.

As noted above, a marker means typically has three markers, although it may have more or less than three markers. It can then transpire that, from the perspective of the detection means, one of the markers obscures another of the markers such that the one marker can no longer be detected or can only be partially detected by the detection means, e.g., as viewed from the detection means a second marker lies in an optical shadow of a first marker or is partially covered by said optical shadow.

For a marker means that has three markers, only one marker can be obscured by another marker when all three markers are situated in one plane. If one of the markers is obscured by another marker, the accuracy with which the location of the marker means is detected can suffer significantly and detection can become unreliable. In the medical context, such obscuring should be brought to the attention of the medical personnel and/or the current location of the marker means should not be displayed.

SUMMARY OF THE INVENTION

A marker means that includes three markers defines a plane, wherein the plane intersects the markers (the three markers span the plane). Within a predetermined spatial angle, through the center of which a vector located normally on the plane passes, it is possible to detect all three markers if the detection means is situated within this spatial angle. A controller could refer to such a condition in order to emit a warning signal if the detection means is not situated within this spatial angle or leaves this spatial angle. However, limiting the operational capability of a marker navigation device in this way does not use all the possible locations for detecting all the markers. Even if the detection means is situated in the same plane as the three markers, e.g., at a spatial angle of 90 degrees, there are still relative locations between the marker means and the detection means at which all three markers are detectable by the detection means.

The present invention provides a marker navigation device that allows a location of a marker means to be determined and/or tracked, wherein the marker means is attachable to an object, such as a body structure (e.g., a bone or cartilage) or a (medical) instrument. Determining the location of the marker means allows the location of the object to also be determined. The location can be determined continuously or intermittently, such that the location of the marker means and, thus, the object, can be tracked.

The location of the marker means can be determined by the position of the marker means in a predetermined reference system. The reference system can be a reference system in which the detection means lies. The location of the marker means can be determined by the positions of the markers, in particular the center points of the markers, in the reference system. The positions, for example, can be described using Cartesian coordinates or spherical coordinates. The location of one part (e.g., the detection means) relative to another part (e.g., the marker means) can be described by spatial angles, distances, coordinates (in a reference system) and/or vectors and can be calculated from the positions describing the location, e.g., by means of a program running on a computer.

The term "relative location" as used herein or the expression "location of a part A relative to a part B" comprises the concept of the relative positions between the two parts, e.g., between the markers or between a marker and the detection means. In particular, centers of gravity or center points of the parts can be selected as a punctiform reference point for establishing a position. If the position of one part is known in a reference system, then it is possible, on the basis of the relative location of two parts, to calculate the position of one of the two parts from the position of the other of the two parts.

If the marker means only comprises two markers, a start position is preferably known, and the marker navigation device then allows the location of the marker means to be tracked when the marker means is spatially moved.

The marker means preferably comprises at least two markers, and more preferably three markers. The dimensions of the markers and the location of the markers relative to each other may be known and/or available as prior-known data of a data processing means. The shape of the markers is preferably also known.

The marker navigation device also can include a detection means that detects signals from the at least two markers. As stated above, these may be signals emitted from the markers that are either actively emitted by the markers or reflected by the markers. In the latter case, a signal transmitting source, for example an ultrasound source or an infrared light source, is preferably also provided that emits signals (e.g., ultrasound pulses or infrared light) towards the passive markers, wherein the passive markers reflect the signals. A data processing means, such as a computer, allows the location of the marker means relative to the detection means to be calculated, in particular the location of the marker means in a reference system in which the detection means lies, e.g., in a reference system that lies in an operating theater.

As already stated above, there may be relative locations between the markers of the marker means and the detection means at which not all the markers are detectable (e.g., locations where detection is impossible) and/or at which the signals emitted from the markers are not clearly distinguishable from each other, e.g., detection is impaired. Such relative locations are referred to here as first relative locations. Detection impairment here means that the signals emitted from both markers at least partially overlap and/or are detected simultaneously on one or more signal-sensitive elements of the detection means. In the optical case, the electromagnetic radiation (light or infrared light) emitted from both markers may be simultaneously measured at least partially by one or more photosensitive elements. Impairment also means that the signals emitted from one marker are weakened by another marker. This may be the case when the radiation or waves emitted from one marker are at least partially blocked by the other marker e.g., one marker is at least partially situated in the shadow of the other marker, from the perspective of the detection means.

Depending on the implemented data processing technique (e.g., pattern recognition), an overlapping signal from the perspective of the detection means can be enough to enable separation of the signals from two markers to a sufficient extent. A clear distance between the markers, however, also can be necessary, such that, for example, detection elements that do not receive signals lie between first detection elements that receive signals from a first marker and second detection elements that receive signals from a second marker.

The first relative locations also can be understood to mean those locations at which it is still possible to separate the signals, but would no longer be possible if the marker means were further shifted to a predetermined extent and in a predetermined way. This also may be understood as an impairment, as there is a danger that the location of the marker means cannot be reliably determined or its location tracked. The first relative locations therefore preferably comprise a "safety corridor" (e.g., a space between a second and first boundary surface), so as to advise the operator in good time of a possible interruption to the display of a location of the marker means.

The remaining relative locations between the markers of the marker means and the detection means, which are not first relative locations and/or allow all the markers to be detected, are referred to as second relative locations.

In the aforementioned "safety corridor", it is still possible to separately detect the markers, but this would no longer be possible if the marker means were further shifted to a particular extent (and in a particular direction).

The relative locations between the marker means and the detection means can be calculated by means of the data processing means. The calculation can be made on the basis of the known dimensions of the markers of the marker means and the known relative locations between the individual markers of the marker means (e.g., on the basis of the distances of the markers and the angles of the triangle whose corners are the center points of the markers). As the detection means preferably comprises two spatially separated detectors (e.g., two cameras), spatial perception is possible, and the actual (current) relative location between the marker means and the detection means can be determined on the basis of detection signals, more precisely on the basis of the detected distances between the markers and the detected angles of the aforementioned triangle.

If the first and second relative locations and the actual relative location are then known, the actual relative location then can be compared with the first and/or second relative locations so as to determine whether the actual relative location is one of the second relative locations and/or one of the first relative locations. This can be determined by means of the data processing means. The first and/or second relative locations can be defined by geometric sizes (e.g., angles) and/or figures (e.g., cone, cylinder), as discussed in more detail below. In particular, the first relative locations can be described by geometric figures (e.g., a cone) in a reference system in which the marker means lies.

The marker navigation device preferably comprises a warning apparatus that can be formed such that it outputs a message. This message can comprise the output of a communication, for example an alarm signal, if the actual relative location is a first relative location, e.g., one of the markers is covered by the other. Additionally or alternatively, the message output can be configured such that the actual relative location are prevented from being communicated, e.g., not displayed (on a monitor). The monitor then can display only a black screen or a warning indication.

In the following, properties of the first relative locations are described by way of example. The first relative locations preferably lie on straight lines that pass through at least two of the markers. In particular, they lie within two apexes whose boundary surfaces are formed by straight lines that touch the edge of the circular cross-section of two markers and intersect at a point that lies on a line connecting the center points of the two spheres. In particular, the intersecting point of the straight lines (i.e., the apexes) lies in the center between the two spheres, if the spheres are formed the same size.

The markers also can lie on straight lines that pass through at least one of the markers and pass by another marker at a predetermined distance. If the straight lines pass by the markers at a predetermined distance, a certain safe distance ("safety corridor") arises that allows the operator to identify at an early stage that one of the markers will possibly be obscured if the marker means is further moved such that one of the markers passes into the shadow of the other.

A safety corridor arises if the first relative locations lie on straight lines that pass by the markers at a predetermined distance or at a distance that is less than the predetermined distance. The predetermined distance preferably lies in a range of up to three times the diameter of the marker, more preferably in a range of up to a whole, a half or a quarter of the marker diameter. The predetermined distance can be in a range of greater than 10%, or greater than 50% of the marker diameter.

The first relative locations also can be described as lying within an imaginary boundary surface, wherein the boundary surface is preferably configured such that it surrounds the markers, and wherein the boundary surface preferably touches at least one of the two markers. Alternatively, the boundary surface also can pass at a predetermined distance from at least one of the two markers. Examples of a predetermined distance have already been cited above. An example of an aforementioned safety corridor can be described as a boundary surface (core boundary surface) surrounding a core area, if it touches the two markers. The intermediate space between this core boundary surface and a boundary surface that passes at a predetermined distance from the markers can be used as a safety corridor. If, due to the movement of the marker means, the actual location of the detection means relative to the marker means enters the safety corridor, then a warning signal can be emitted. If the movement continues and the actual relative location enters the area of the core boundary surface, the actual relative location then can be prevented from being displayed and/or another, in particular more intense, warning signal can be emitted. If the markers are spherical, the aforementioned boundary surface can assume a cylindrical shape, particularly if the detectors are "monocular". However, as already stated above, (at least) two detectors are preferably provided in the detection means. In this case in particular, a boundary surface area may be tapered between the markers and can be described by two cones that touch at their tips and have cone axes that merge into each other.

The marker means is preferably formed such that the actual relative location (calculated on the basis of the current detection signals) is displayed even when the detection means and the marker means are located in the same plane but the detection means does not assume a first relative location. In other words, there can be second relative locations which lie in the same plane as that established by the markers.

BRIEF DESCRIPTION OF THE DRAWINGS

The forgoing and other features of the invention are herein after discussed with reference to the drawing.

DETAILED DESCRIPTION

Figure 1:
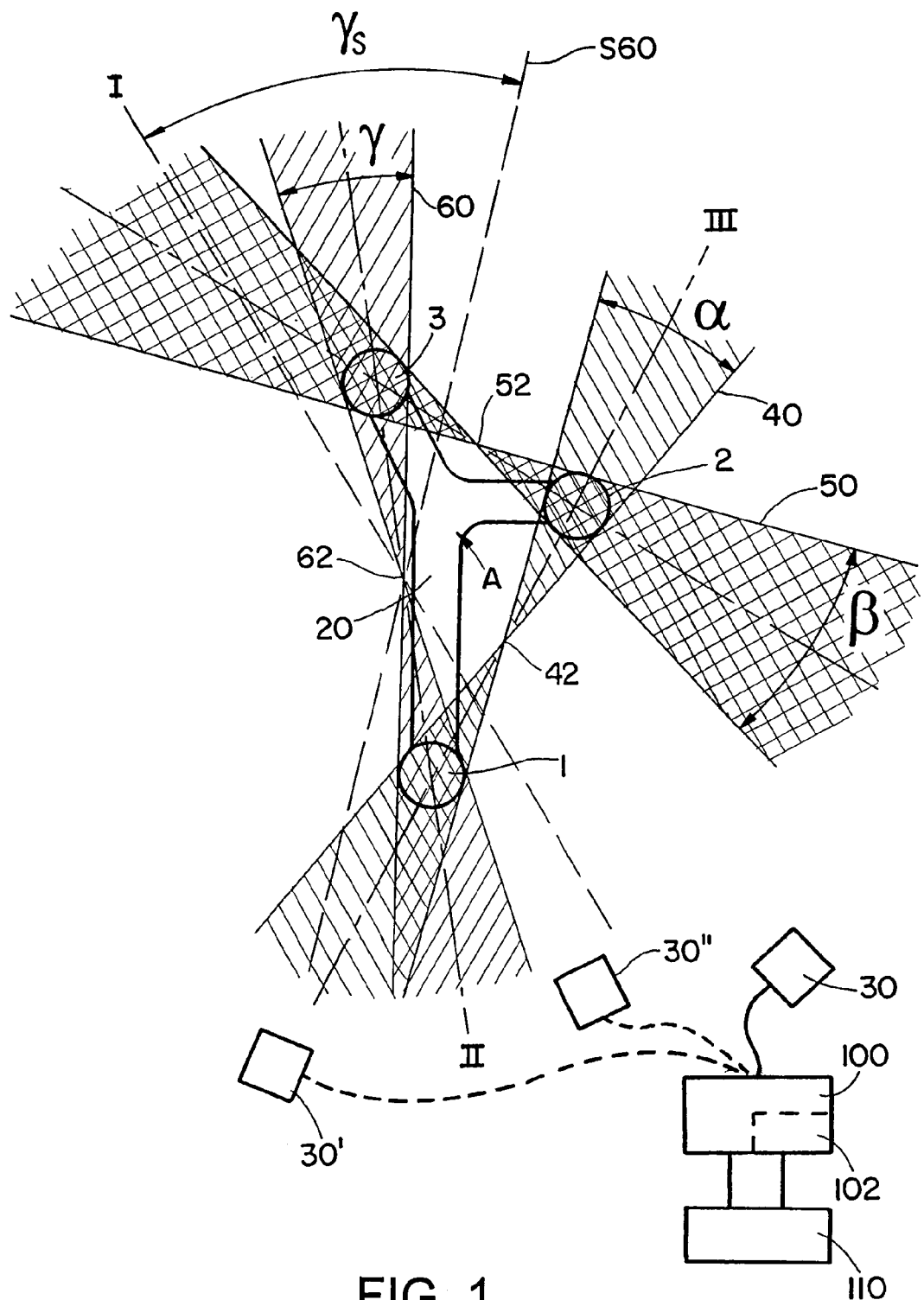
FIG. 1 shows an exemplary marker navigation device in accordance with the invention.

An exemplary marker navigation device is shown in FIG. 1 and comprises a reference star 20 with marker spheres 1, 2 and 3 connected by a bar A. The reference star 20 represents an example of a marker means. The marker spheres, which in the present example are passive marker spheres that do not emit radiation themselves but reflect radiation or waves, are detected by a detection means 30 (e.g., a camera or the like). Three example positions of the detection means 30 are indicated in FIG. 1. The first position is provided with the reference sign 30, the second position with the reference sign 30', and the third position with the reference sign 30".

Cone-shaped boundary surfaces bearing the reference signs 40, 50 and 60 surround the marker spheres 1, 2 and 3. The cone-shaped boundary surface 60 relates to the marker spheres 1 and 3, the cone-shaped boundary surface 40 relates to the marker spheres 2 and 1, and the cone-shaped boundary surface 50 relates to the marker spheres 2 and 3. The cone-shaped boundary surfaces are formed and/or spanned by straight lines that touch the outer side of the marker spheres and intersect in the center between two marker spheres on an axis that passes through the center point of the marker spheres (e.g., at points 42, 52 and 62). The axes that pass through the center points of the marker spheres also represent the central axes of the cone-shaped boundary surfaces that are formed in rotational symmetry around these axes. The axes are indicated by I, II and III.

If the detection means is situated in the position indicated by 30, then none of the marker spheres obscures the other. However, if it is located in the position indicated by 30', then marker sphere 1 obscures marker sphere 2. In other words, marker sphere 2 is located in the shadow of marker sphere 1. In this case, it is no longer possible to detect all the marker spheres, and the actual relative location of the marker means is preferably not displayed.

The actual relative location of the detection means 30 can be calculated using a data processing means 100, such as a computer or the like. The data processing means 100 can be connected to the detection means 30 in an electrical and/or signal connection. The data processing means 100 outputs the calculated data to a display means 110, which displays the actual relative location, provided such display is not prevented by the warning apparatus 102 (which can be implemented by a software program and run on the data processing means 100). As an alternative to or in addition to the display means 110, the actual location can be communicated acoustically, for example.

The cones surrounded by the boundary surfaces 40, 50 and 60 enclose the spatial angles $\alpha$, $\beta$, and $\gamma$, respectively. As can be seen from FIG. 1, the spatial angles $\alpha$, $\beta$, and $\gamma$ are different. This is due to the different distances between the marker spheres 1 and 3, the marker spheres 3 and 2, and the marker spheres 2 and 1.

In FIG. 1, S60 indicates a boundary surface that surrounds the boundary surface 60 (in rotational symmetry). The boundary surface S60 spans a spatial angle $\gamma_s$. The boundary surface S60 circumscribes a safety corridor situated between the boundary surface 60 and the boundary surface S60. When the detection means is in the position indicated by 30", it is possible to detect all three marker spheres. However, detection is at risk if the marker means continues to move such that the detection means 30 enters the boundary surface 60. In this position, a warning signal can be output that indicates that it may no longer be possible to display the locations if the movement continues. The safety corridor shown in FIG. 1 lies outside the spatial angle but within the spatial angle $\gamma_s$.

The aforementioned boundary surface S60 is also referred to here as a first boundary surface, and the aforementioned boundary surfaces 40, 50 and 60 are referred to as second boundary surfaces. The aforementioned "safety corridor" is thus the space between the first boundary surface S60 and the second boundary surface 60. The first boundary surfaces are preferably configured such that in a plane spanned by the marker spheres, second relative locations are provided that lie outside the first boundary surfaces but are situated in this plane. In FIG. 1, the second relative locations are those which are situated outside the boundary surface areas 40, 50 and S60.

Figure 2:
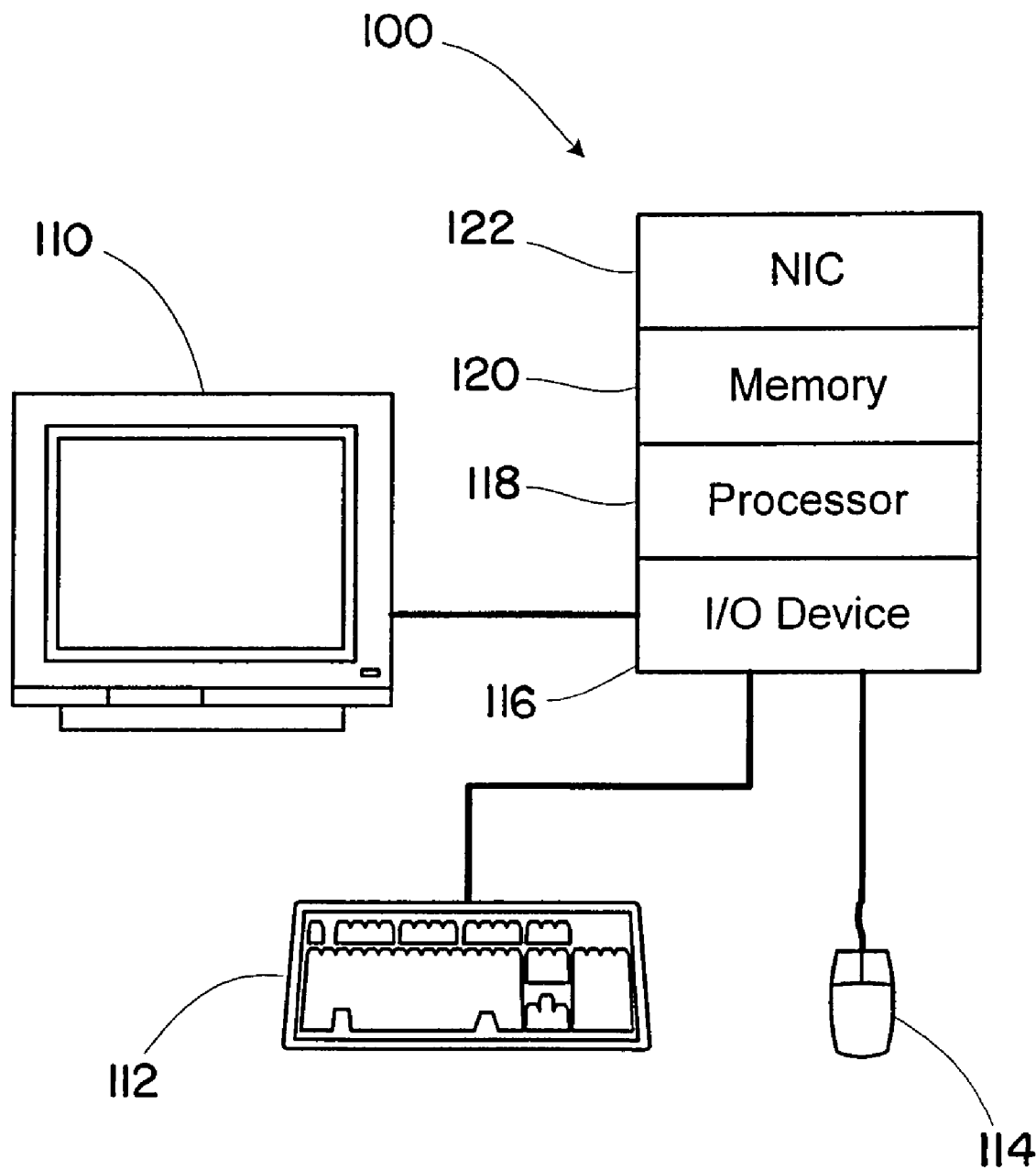
FIG. 2 is a block diagram of an exemplary computer system that may be used to carry out one or more of the methods described herein.

Moving now to FIG. 2 there is shown a block diagram of an exemplary computer 100 that may be used to implement one or more of the methods described herein. The computer 100 may include a display 110 for viewing system information, and a keyboard 112 and pointing device 114 for data entry, screen navigation, etc. A computer mouse or other device that points to or otherwise identifies a location, action, etc., e.g., by a point and click method or some other method, are examples of a pointing device 114. Alternatively, a touch screen (not shown) may be used in place of the keyboard 112 and pointing device 114. The display 110, keyboard 112 and mouse 114 communicate with a processor via an input/output device 116, such as a video card and/or serial port (e.g., a USB port or the like).

A processor 118, such as an AMD Athlon 64® processor or an Intel Pentium IV® processor, combined with a memory 120 execute programs to perform various functions, such as data entry, numerical calculations, screen display, system setup, etc. The memory 120 may comprise several devices, including volatile and non-volatile memory components. Accordingly, the memory 120 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 118 and the memory 120 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 122 allows the computer 100 to communicate with other devices, such as the detection device 30, for example.

A person having ordinary skill in the art of computer programming and applications of programming for computer systems would be able in view of the description provided herein to program a computer 100 to operate and to carry out the functions described herein. Accordingly, details as to the specific programming code have been omitted for the sake of brevity. Also, while software in the memory 120 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A marker navigation device for determining or tracking a location of a marker device attachable to an object, said marker device including a plurality of markers having known dimensions and being in a known positional relationship relative to each other, comprising:
   a detection device operative to detect signals emitted by or reflected from the plurality of markers, wherein
      in first locations of the detection device relative to the marker device, detection of signals from one marker of the plurality of markers is restricted or impossible due to a location of another marker of the plurality of markers, and
      in second locations of the detection device relative to the marker device, the plurality of markers are detectable by the detection device;
   a processing device communicatively coupled to the detection device and configured to
      calculate the first relative locations based on the relative locations of individual markers of the plurality of markers and based on the known dimensions of the plurality of markers, and
      calculate an actual location of the marker device relative to the detection device based on detected signals from at least one marker of the plurality of markers, the known locations of the plurality of markers relative to each other, and the known dimensions of the plurality of markers, and
      determine whether the actual relative location of the marker device is one of the first locations; and
   a warning device communicatively coupled to the processing device and operative to output a warning signal when the actual relative location is one of the first relative locations.

2. The marker detection device according to claim 1, wherein the first relative locations meet at least one of the following conditions:
   a) the first relative locations lie on straight lines that pass through at least two markers of the plurality of markers;
   b) the first relative locations lie on straight lines that pass through a first marker of the plurality of markers and pass by a second marker of the plurality of markers at a predetermined distance or less than the predetermined distance; or
   c) the first relative locations lie on straight lines that pass by two markers of the plurality of markers at a predetermined distance or less than the predetermined distance.

3. The marker detection device according to claim 1, wherein the first relative locations lie on straight lines that intersect between two markers of the plurality of markers.

4. The marker detection device according to claim 1, wherein the first relative locations lie within an imaginary boundary surface that surrounds two markers of the plurality of the markers and touches at least one marker of the plurality of markers or passes at a predetermined distance from at least one marker of the plurality of markers.

5. The marker detection device according to claim 4, wherein the boundary surface exhibits a narrowest cross-sectional area or a cross-sectional point, from which the boundary surface continuously widens between the two markers of the plurality of markers.

6. The marker detection device according to claim 4, wherein the markers exhibit a round cross-section and the boundary surface is cone-shaped.

7. The marker detection device according to claim 1, wherein the warning device is operative to output a first message if the actual relative location is one of the first relative locations and lies within a first imaginary boundary surface but not within a second imaginary boundary surface, and the warning device is operative to output a second message if the actual relative location lies within the second boundary surface, wherein the first boundary surface surrounds the second boundary surface, at least the first and second boundary surfaces surround the two markers of the plurality of markers.

8. The marker detection device according to claim 7, wherein the first message differs from the second message.

9. The marker detection device according to claim 7, wherein the first boundary surface is a predetermined distance from the plurality of markers.

10. The marker detection device according to claim 1, comprising a display apparatus for displaying a location corresponding to the calculated actual relative location of the marker device.

11. The marker detection device according to claim 10, wherein the display apparatus displays the location if a) the plurality of markers are situated in one plane and b) the actual location is one of the second relative locations.

12. The marker detection device according to claim 1, wherein outputting the warning signal includes the warning device communicating an alarm signal or preventing the actual relative location from being output.

13. The marker detection device according to claim 1, further comprising the marker device.

14. A method for detecting a marker device attachable to an object, wherein the marker device comprises a plurality of markers having known dimensions and known locations relative to each other, wherein in first locations of a detection device relative to the marker device, detection of signals emitted by or reflected from at least one marker of the plurality of markers is restricted or impossible due to a location of another marker of the plurality of markers, and in second locations of the detection device relative to the marker device, the plurality of markers are detectable by the detection device, comprising:

calculating first relative locations based on the relative locations between individual markers of the plurality of markers and based on the dimensions of the plurality of markers;

calculating an actual location between the marker device relative to the detection device based on the detected signals, the known locations of the plurality of markers relative to each other and the known dimensions of the plurality of markers;

determining whether the actual relative location is one of the first relative locations; and outputting a message if the actual relative location is one of the first relative locations.

* * * * *